United States Patent [19]

Pursley

[11] Patent Number: Plant 6,529

[45] Date of Patent: Jan. 10, 1989

[54] ZOYSIA GRASS PLANT CV 'P-1'

[76] Inventor: Walter L. Pursley, 1038 - 41st Ave. North, St. Petersburg, Fla. 33703

[21] Appl. No.: 27,620

[22] Filed: Mar. 18, 1987

[51] Int. Cl.[4] ..... A01H 5/00
[52] U.S. Cl. ..... Plt./88
[58] Field of Search ..... Plt./88

*Primary Examiner*—James R. Feyrer

[57] ABSTRACT

I disclose that my herein invention of a new variety of Zoysia grass plant was discovered by me in a sod field at Manatee County, State of Florida. This new discovered Zoysia grass plant is a perennial, which exhibits an attractive dark yellowish-green color, color No. 137, of a finer softer texture, that produces outstanding vigorous stolon growth with excellent green winter color retention. The anthers are dark purplish-red color, color No. 259.

1 Drawing Sheet

The present invention relates to a new and distinct variety of Zoysia grass plant which was discovered by me, growing as a newly found seedling of unknown parentage growing in a cultivated turf plot and brought to my grass farm in Manatee County, State of Florida. I observed that this variety of Zoysia Matrella grass had a finer softer texture and was producing a more noticeable vigorous growth, forming a distinct patch area in the large field of Emerald Zoysia grass, overtaking and crowding out the Emerald Zoysia grass. I broke off several stolons of this newly discovered Zoysia grass plant, which I designated P-1. I transplanted the stolon pieces I broke off of the new variety of Zoysia grass, in a prepared area for further trials and testing, so as to observe the characteristics of this new variety of Zoysia grass. As this area planted by me became established through regular fertilizing, watering and mowing, I observed again that the new variety of Zoysia grass produced a more vigorous stolon growth rate when compared to the closest known variety, Emerald Zoysia grass which was measured at a randomized replicated trial, at a 40% to 50% greater stolon growth rate when measured over a full coverage period. This new variety of Zoysia grass was also finer and softer in texture; then during the winter period, exhibited superior color retention when compared to Emerald Zoysia grass. The root systems of the claimed variety of Zoysia grass, and the closest known variety of Zoysia grass plant, do not show noticeable differences. The new claimed variety of Zoysia grass plant, produces seeds that are variable in seedling character and of low germination. Continued asexual reproduction by me, through stolons and rhizomes of this new variety of Zoysia grass plant, have confirmed that the above characteristics are transmitted through succeeding propagations and have confirmed that the new Zoysia grass plant has the following unique combination of characteristics.

Figure 1:
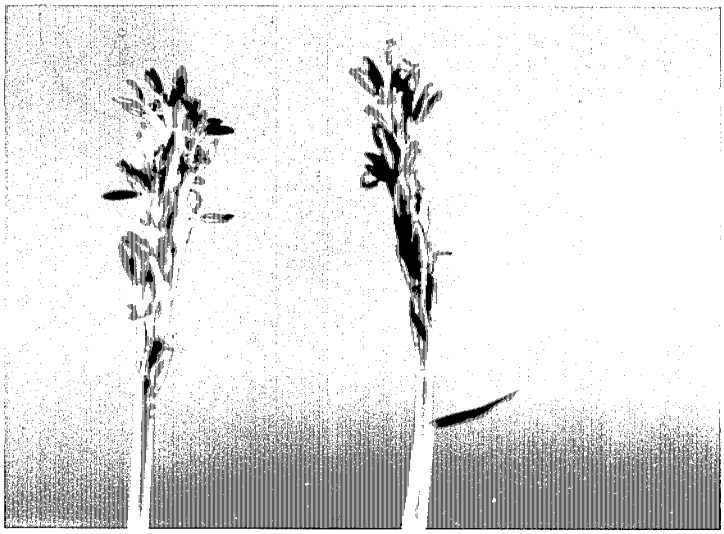
FIG. 1. Is a photograph of two spikes taken from the same test area. The spike in the right of the photograph is of the new claimed variety of Zoysia grass plant, showing anthers of dark purplish-red color, Color No. 259. Compared to the closest known variety of Zoysia grass plant, Emerald Zoysia grass plant, which is in the left of this photograph showing anthers of grayish purplish-red color, Color No. 262.
Figure 2:
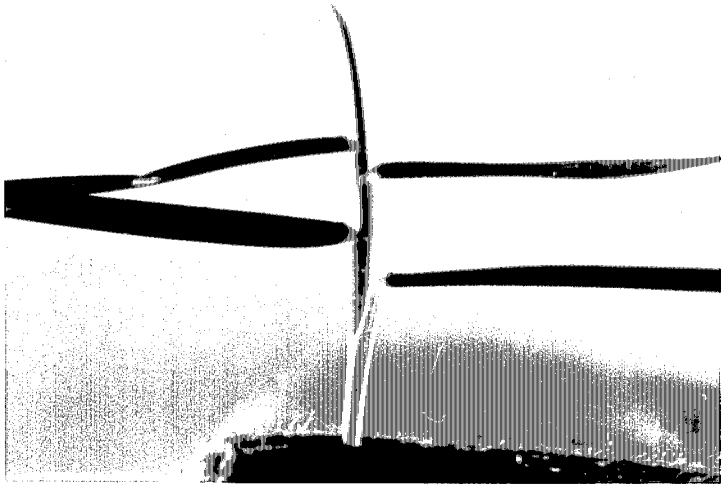
FIG. 2 is a photograph of a culm taken from the same test area of the new claimed variety of Zoysia grass plant. This photograph shows the glabrous leaf blades and sheath.
Figure 3:
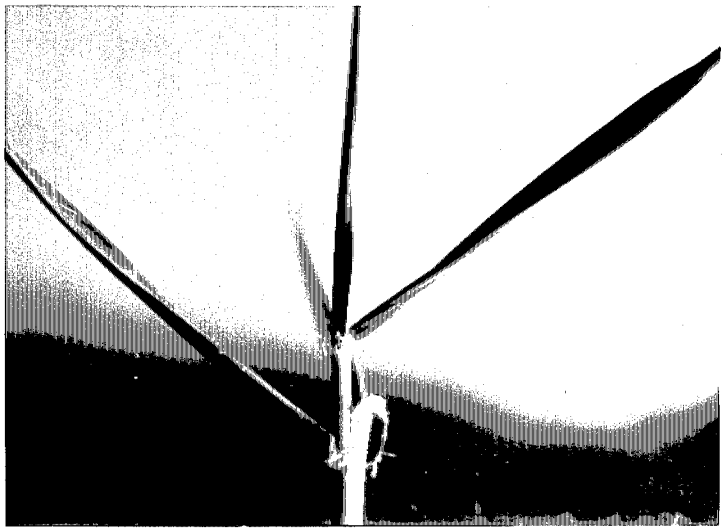
FIG. 3 is a photograph of a culm taken from the same test area of the closest known variety of Zoysia grass plant, Emerald Zoysia grass plant. This photograph shows the pubescent upper leaf surface with long hairs at the ligule and sheath.

The following is a detailed description of my new claimed Zoysia grass plant variety, with color terminology in accordance with the ISCC-NBS Centroid Color Chart, except where general color terms of ordinary dictionary significance are obvious. The grass is:

(a) An attractive dark yellowish green color, Color No. 137.

(b) The grass is low-growing stoloniferous, rhizomatous and fast establishing.

(c) Leaves are rolled in bud shoot.

(d) The leaf blade is glabrous, flat and gradually tapering to an acute point.

(e) Culms are 9–11 centimeters long.

(f) Ligule is a small ciliate fringe.

(g) Auricles are absent.

(h) Collar is broad continuous.

(i) Sheath is glabrous, except for 2–3 hairs at the top of the sheath at the sides of the ligule.

(j) The first mature leaf is 1–1.5 millimeters in width and 4–5 centimeters long.

(k) The stolon nodes are 14–18 millimeters apart.

(l) The entire plant is glabrous, except at the top of the sheath at the sides of the ligule where 2–3 hairs are present.

(m) The inflorescence consists of a single spike at the top of the main stem with anthers of dark purplish red color, Color No. 259., and stigmas of pale yellow green color, Color No. 121.

A detailed description of the closest known variety of the species of Zoysia grass plant, which is known as Emerald, is:

(a) The grass color is a moderate olive green color, color No. 125.m.OL G.

(b) The grass is low-growing, stoloniferous, rhizomatous and slow establishing.

(c) Leaves rolled in bud shoot.

(d) The leaf blade is pubescent on the upper leaf surface, flat and gradually tapering to an acute point.

(e) Culms are 16–20 centimeters long.

(f) Ligule is a small ciliate fringe with a ring of hairs.

(g) Auricles are absent.

(h) Collar is broad continuous.

(i) Sheath is glabrous, except at the top of the sheath where it is densely pubescent.

(j) The first mature leaf is 1.5–2.5 in width and 3–7 centimeters long.

(k) The stolon nodes are 20–25 millimeters apart.

(l) The entire plant is glabrous, except on the upper leaf surface, which is pubescent, and the sheath is densely pubescent at the top of the sheath at the side of the ligule.

(m) The inflorescence consists of a single spike at the top of the main stem with anthers of grayish purplish red color, Color No. 262, and stigmas of pale yellow green color, Color No. 121.

I claim:

1. A new and distinct variety of Zoysia grass plant, substantially as herein described and illustrated, characterized particularly by fast stolon and rhizome establishment, and of a softer finer texture, with excellent green color retention in the winter period; the new claimed Zoysia grass plant is almost entirely glabrous, of dark yellowish green color, color No. 137, with anthers of dark purplish red color, color No. 259.

* * * * *